United States Patent

Johnson et al.

[11] Patent Number: 6,051,636
[45] Date of Patent: Apr. 18, 2000

[54] ENTRAPMENT OF NUCLEIC ACID SEQUENCING TEMPLATE IN SAMPLE MIXTURES BY ENTANGLED POLYMER NETWORKS

[75] Inventors: Ben F. Johnson, Palo Alto; Steven M. Menchen, Fremont; Will Bloch, San Mateo, all of Calif.

[73] Assignee: The Perkin-Elmer Corporation, Foster City, Calif.

[21] Appl. No.: 09/264,757

[22] Filed: Mar. 9, 1999

Related U.S. Application Data

[63] Continuation of application No. 08/554,247, Nov. 8, 1995, Pat. No. 5,891,313, which is a continuation-in-part of application No. 08/349,229, Dec. 5, 1994, abandoned, which is a continuation-in-part of application No. 08/156,218, Nov. 23, 1993, abandoned.

[51] Int. Cl.[7] .................... C08K 5/151; C08K 5/3415
[52] U.S. Cl. .................... 524/98; 204/601; 204/451; 524/104; 524/99; 524/733; 524/110; 524/111
[58] Field of Search .................. 524/104, 98, 99, 524/733, 110, 111, 827, 831; 527/103; 106/173.01, 174.1; 204/601, 451; 435/6; 536/123.1

[56] References Cited

U.S. PATENT DOCUMENTS

| | | |
|---|---|---|
| 4,911,807 | 3/1990 | Burd . |
| 5,055,517 | 10/1991 | Shorr et al. . |
| 5,085,756 | 2/1992 | Swedberg . |
| 5,096,554 | 3/1992 | Chin . |
| 5,126,021 | 6/1992 | Grossman .................. 204/601 |
| 5,164,055 | 11/1992 | Dubrow . |
| 5,374,527 | 12/1994 | Grossman .................. 204/451 |
| 5,455,344 | 10/1995 | Harper et al. .............. 536/123.1 |
| 5,552,028 | 9/1996 | Madabhushi et al. . |
| 5,567,292 | 10/1996 | Madabhushi et al. ........ 204/451 |
| 5,874,212 | 2/1999 | Prockop et al. ............... 435/6 |

FOREIGN PATENT DOCUMENTS

| | | |
|---|---|---|
| 0 162 657 | 11/1985 | European Pat. Off. . |
| 0 459 241 | 12/1991 | European Pat. Off. . |
| 0 471 949 | 2/1992 | European Pat. Off. . |
| 0 500 211 | 8/1992 | European Pat. Off. . |
| 0 497 448 | 8/1997 | European Pat. Off. . |
| WO 94/14824 | 7/1994 | WIPO . |
| WO 95/06668 | 3/1995 | WIPO . |
| WO 95/14921 | 6/1995 | WIPO . |
| WO 95/14922 | 6/1995 | WIPO . |

*Primary Examiner*—Robert Dawson
*Assistant Examiner*—Kuo-Liang Peng
*Attorney, Agent, or Firm*—Paul D. Grossman

[57] ABSTRACT

A capillary electrophoresis system and method of electrokinetically loading a capillary electrophoresis sample into a separation medium in a capillary tube in which an entangled polymer matrix is formed having the sample embedded therein. The matrix has a mesh size effective to retard movement of macromolecules such as DNA sequencing templates through the matrix when an electric field is applied across the matrix. The entangled polymer matrix is formed by a linear polymer having a molecular weight of at least 20K Daltons. Furthermore, the invention includes stable denaturants useful for the electrophoresis of nucleic acids.

7 Claims, 6 Drawing Sheets

ENTRAPMENT OF NUCLEIC ACID SEQUENCING TEMPLATE IN SAMPLE MIXTURES BY ENTANGLED POLYMER NETWORKS

RELATED U.S APPLICATIONS

This application is a continuation of U.S. application Ser. No. 08/554,247, filed on Nov. 8, 1995, now U.S. Pat. No. 5,891,313, which is a continuation-in-part of U.S. application Ser. No. 08/349,229, filed on Dec. 5, 1994, now abandoned, which is a continuation-in-part of U.S. application Ser. No. 08/156,218, filed on Nov. 23, 1993, now abandoned.

FIELD OF THE INVENTION

This invention generally relates to capillary electrophoresis of nucleic acids such as DNA, and more particularly to a sample preparation technique to restrict the mobility of nucleic acid templates in a sample solution.

DESCRIPTION OF THE RELATED ART

Gel electrophoresis is a powerful method of separating large biomolecules, such as proteins, deoxyribonucleic acids (DNA), and ribonucleic acids (RNA). In gel electrophoresis, a mixture of biomolecules is placed on a selected gel medium and the gel is subjected to an external electric field. The velocity (v) of migration of a biomolecule through the gel depends on the strength of the electric field (E), the net charge (z) on the molecule, and the frictional coefficient (f) of the medium:

$$v = Ez/f$$

The frictional coefficient depends on the mass and shape of the molecule, the viscosity, and the porosity of the medium.

Gels have become the preferred medium for conducting electrophoretic separations because they suppress the convective currents produced by small temperature gradients in less viscous media, and they act as molecular sieves which inhibit movement of large molecules, but permit smaller molecules to move readily through the pores of the gel, thereby effecting a sizedependent separation. Polyacrylamide gels have generally been the medium of choice for performing separations because they are chemically inert and their pore sizes can be controlled by selection of a desired ratio of acrylamide and methylenebisacrylamide (cross-linking agent), and of the total monomer concentration used in polymerization. The polyacrylamide gel is typically generated by free-radical polymerization of the component monomers, using a free-radical initiator, in the presence of the electrophoresis medium.

Electrophoretic separations of proteins are often performed in a cross-linked polyacrylamide gel under protein denaturing conditions. For example, proteins can be dissolved in a detergent solution, e.g., sodium dodecyl sulfate (SDS), and subjected to mercaptoethanol or dithiothreitol treatment to reduce any disulfide bonds. The SDS anions bind to the protein at a ratio of about one SDS molecule to two amino acid residues, thereby imparting a large net negative charge and bulk to the denatured protein. The charge and bulk of the protein-SDS complex are roughly proportional to the mass of the native protein. Displacements of a protein or peptide within a gel matrix can thereby be related to molecular size on a basis of the size and charge on the molecule. In the case of nucleic acids, which have roughly a size-independent charge density, displacement in the gel matrix is more directly related to molecular size.

Electrophoresed complexes are usually visualized by staining with a dye, such as Coomassie blue, or by autoradiography when the molecules are radioactively labeled. The displacement of a biomolecule in the gel is nearly linearly proportional to the logarithm of the mass of the molecule, with exceptions found for such species as glycosylated and membrane proteins. Proteins differing by as little as 2% in mass can often be distinguished by electrophoresis.

One electrophoretic technique that permits rapid, high resolution separation is capillary electrophoresis (CE). In one CE procedure, a capillary tube is filled with a fluid electrophoresis medium and the fluid medium is crosslinked or temperature-solidified within the tube to form a non-flowable, stabilized separation medium. A sample volume is draw into one end of the tube by electrokinetic injection, and an electric field is applied across the tube to draw the analytes through the medium. Typically, a bioseparation conducted by CE employs fused silica capillary tubes having inner diameters between about 50–200 microns, and ranging in length between about 10–100 cm or more.

The polymer concentration and/or degree of cross-linking of the separation medium may be varied to provide separation of species over a wide range of molecular weights and charges. For example, in separating nucleic acid fragments greater than about 1,000 bases, one preferred temperature-solidified material is agarose, where the concentration of the agarose may vary from about 0.3%, for separating fragments in the 5–60 kilobase size range, up to about 2%, for separating fragments in the 100–3,000 basepair range. Smaller size fragments, typically less than about 1,000 basepairs, are usually separated in cross-linked polyacrylamide. The concentration of acrylamide polymer can range from about 3.5%, for separating fragments in the 100–1,000 basepair range, up to about 20%, for achieving separation in the 10–100 basepair range. For separating proteins, cross-linked polyacrylamide at concentrations between about 3–20% are generally suitable. In general, the smaller the molecular species to be fractionated, the higher is the concentration of cross-linked polymer required.

The resolution obtainable in solidified electrophoresis media of the type described above has been limited, in the case of small molecular weight species, by difficulties in forming a homogeneous, uniform polymer matrix at high polymer concentration within an electrophoresis tube, and especially within a capillary tube. In one general method for forming a high-concentration solidified matrix in a tube, a high concentration polymer solution, in a non-crosslinked, low viscosity form, is introduced in fluid form into the tube. The fluid material is then cross-linked, for example, by exposure to light in the presence of persiflage and a cross-linking agent.

At high polymer concentrations, polymerization reaction heat gradients formed within the tube tend to produce uneven rates of reaction and heat turbulence which can lead to matrix inhomogeneities. Also, entrapped gas bubbles generated during the crosslinking reaction produce voids throughout the matrix. The non-uniformities in the matrix limit the degree of resolution that can be achieved, particularly among closely related, small molecular weight species. These problems may be overcome by polymerizing the gel material at elevated pressure; however, producing a controlled pressure within a capillary gel introduces difficult technical problems.

In the case of temperature-solidified gels, a polymer is introduced into an electrophoresis tube in a fluid form, then allowed to gel to a solid form by cooling within the tube. This approach, however, is generally unsuitable for fractionating low molecular weight species, such as small peptides and oligonucleotides, since the polymers, such as agar and agarose, that are known to have the necessary temperature-solidifying setting properties are not effective for fractionating low molecular weight species, even at high polymer concentrations.

A second limitation associated with crosslinked or temperature-solidified matrices is the difficulty in removing crosslinked gel matrix from the gel support. In the case of a capillary-tube support, this problem may prevent recovery of separated material within the gel, and also may prevent reuse of the capillary tube.

The gel matrix employed in capillary electrophoretic systems has historically generally been a solid gel such as an agarose gel or cross-link polymer matrix, such as a cross-link polyacrylamide matrix. Such gels may be difficult to introduce into the capillary tube without bubbles or voids, and generally preclude reusing the tube. More recently, capillary electrophoresis systems employing a polymer solution as separation medium have been disclosed. U.S. Pat. No. 5,096,554, entitled "Nucleic Acid Fractionation by Counter Migration Capillary Electrophoresis", describes an electrophoresis system in which DNA fractionation occurs in a polymer solution which itself is migrating through the tube by electroosmotic flow in a direction opposite to that of DNA movement in the gel. Another co-owned U.S. Pat. No. 5,164,055, for "High Viscosity Polymer Matrix and Methods", discloses the use of a viscoelastic polymer solution as a substitute matrix for a cross-linked gel matrix in capillary electrophoresis. Another co-owned U.S. Pat. No. 5,126,021, entitled "Low-Viscosity Polymer Solution for Capillary Electrophoresis", discloses a capillary electrophoresis tube containing a low-viscosity polymer solution having a selected mesh size and low solution viscosity. Mesh size may range from 50–100 Angstroms, for separating single-stranded oligonucleotides; to 300 Angstroms or greater for separating relatively large duplex DNA fragments or proteins. Yet another co-owned U.S. patent application Ser. No. 08/003,968 filed Jan. 21, 1993, now U.S. Pat. No. 5,374,527, disclose a capillary-electrophoresis based DNA sequencing method using low-viscosity solutions of linear polyacrylaride. Another co-owned U.S. patent application Ser. No. 08/170,078 filed Dec 17, 1993, now abandoned, discloses a low-viscosity polymer composition which acts as both a sieving agent and a wall-coating agent useful for DNA sequencing. These patents and co-owned patent applications are incorporated herein by reference in their entirety.

More recently, a viscous polymer electrophoresis medium has been developed which is a stabilized gel, easily removed from the capillary tubes, which comprises a matrix of aggregated regular, alternating copolymers in an aqueous medium. The copolymers are composed of hydrophilic polymer segments and hydrophobic polymer segment, wherein the hydophobic segments are separated from one another by the hydrophilic polymer segments. This medium is characterized by 1) the ability of the medium to effect a high-resolution electrophoretic separation of biopolymer molecules in a defined molecular size range; and 2) a concentration of the copolymer which is above the interpolymeric aggregation transition concentration defined by the concentration of copolymer at which a marked rise in viscosity of an aqueous dispersion of the copolymer is observed. The copolymers may have a comb or tuft structure, a block structure, or a star structure, depending on how the hydrophobic polymer chains are arranged. This viscous electrophoresis polymer medium is described in more detail in co-owned U.S. patent application Ser. No. 07/950,863, filed Sep. 24, 1992, now U.S. Pat. No. 5,290,418 which is hereby incorporated by reference in its entirety.

Electrokinetic loading of a liquid nucleic acid sequencing sample mixture containing nucleic acid target, template and partial-sequence nucleic-acid fragment analytes such as DNA primer extension products into a capillary electrophoresis tube filled with a gel medium such as an agarose gel or polymer gel as described above is the preferred method of introducing a sample of analytes into the capillary electrophoresis tube. Electrokinetic loading preferentially introduces the analytes and thus, in effect, concentrates the sample. However, the amount of analyte introduced into the capillary electrophoresis medium is limited by nucleic acid template buildup on the injection end surface of the CE medium in the capillary tube. This template buildup clogs the end of the capillary tube with these large biomolecules and prevents passage of additional analytes into the medium. This phenomenon effectively limits the maximum amount of partial-sequence fragments that can be injected and electrophoresed.

This clogging problem is especially severe in capillary electi-ophoresis, since clogging of the end of the capillary not only blocks entry of sample components, but also causes a series of events that result in extensive bubble formation in the capillary tube which interferes with both the resolution of extension products and the electrical conductivity of the capillary.

For example, the maximum injection time before clogging of a conventional CE capillary tube filled with a comb polymer gel medium, as is described in U.S. Ser. No. 07/950,863, is about 60 seconds at 0.7 kV (0.4 IAA) which is equivalent to 8 seconds at 4.5 kV. This clogging of the capillary electrophoresis tube in turn severely limits the amount of extension product (partial-sequence fragments) that can be resolved during capillary electrophoresis.

One solution to clogging of the end of the capillary tube is to effectively eliminate the template DNA from the sample by depyrimidination with UDG enzyme. This method is described in Swerdlow et al, "Stability of Capillary Gels for Automated Sequencing of DNA", *Electrophoresis* 1992, 13, 475–483. UDG is an enzyme which edits DNA to eliminate occasional uracil residues which may be inadvertently incorporated by DNA. polymerase, or produced by cytosine deamination. According to the Swerdlow method, uricil is incorporated deliberately into the sequencing template during PCR in the presence of a mixture of dUTP and TTP.

Another solution to clogging of the capillary electrophoresis tube is to cut off the template-clogged end of the capillary tube shortly after introduction of the sample. The cut end thus presents a new end surface for introducing the buffer and/or analytes from the run underway as well as for the next sample to be introduced into the tube. This step is unsatisfactory in that only a few samples can be run sequentially through the same capillary tube before the shortening of the capillary length adversely affects resolution and reproducibility of DNA fragment separation. Alternatively, a new tube may be utilized for each sample.

SUMMARY OF THE INVENTION

It is an object of the present invention to provide a method of increasing the amount of analyte or analytes in the liquid sample that can be introduced into the entrance end of the capillary electrophoresis tube.

It is another objective of the present invention to provide a method of retarding the migration of large macromolecules in the sample solution, thereby lengthening the time during which smaller biomolecules may be introduced into the electrophoretic medium.

It is a still further object of the invention to provide a capillary electrophoresis system which enhances the resolution of partial-sequence DNA fragments by having the sample mixture embedded in an entangled polymer matrix effective to retard movement of the template DNA during electrokinetic introduction of the partial-sequence DNA fragments into the capillary tube.

It is another object of the present invention to provide a nucleic acid denaturant solution which is stable in aqueous solution.

These and other objects of the invention are achieved by formulating an open entangled or aggregate polymer network in a DNA sequencing sample mixture containing DNA template and DNA extension products. The polymer matrix is a structured network stabilized by entanglement or by micellar interactions. The sample constituents are then introduced into a capillary electrophoresis tube by electrokinetic injection.

More specifically, these and other objects of the invention are preferably achieved by introducing a small concentration of a long linear polymer solution into the DNA sequencing sample mixture before electrokinetic loading or injection of the analytes into the capillary tube. This long linear polymer solution creates an open entangled polymer network or matrix as described in U.S. Pat. No. 5,126,021 into which the sample mixture containing the DNA template macrobiomolecule and biomolecules such as DNA extension products integrates or becomes embedded. This open entangled polymer network retards the mobility of the DNA template macrobiomolecules while effectively allowing free passage of the smaller biomolecules such as the partial-sequence fragments e.g. DNA extension products. In effect, the open entangled polymer network or matrix has sieving properties that preferentially restricts movement of large biomolecules having a size greater than about 2000 bases or base-pairs (bp). The long linear polymer selected is preferably hydroxyethylcellulose (BEC) with a molecular weight of between $2\times10^5$ and $5\times10^6$ Daltons. Chemically similar polymers may also be utilized.

Preferably the DNA sequencing sample mixture includes a denaturant sufficient to denature double-stranded DNA at room temperature, i.e., to render the double-stranded DNA single stranded. Preferred denaturants include urea, dimethylformamide, lactarn, and lactone. More preferably, the denaturant is 2-pyrrolidinone.

DETAILED DESCRIPTION OF THE INVENTION

Figure 1:
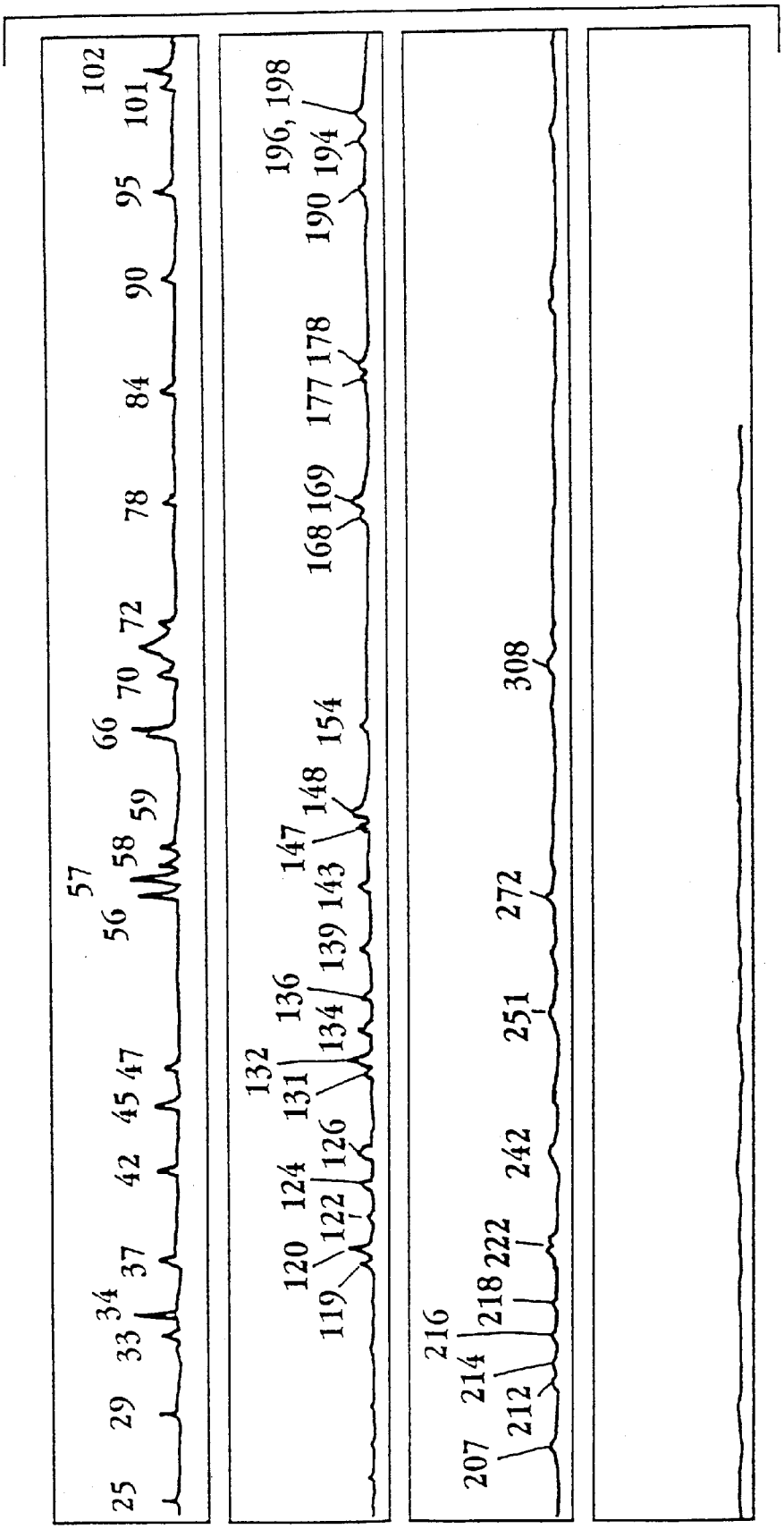
FIG. 1 is an electropherogram of the results of control Example 1.

The system and method in accordance with the invention basically entraps macrobiomolecules in a sample mixture containing macrobiomolecules and biomolecule analytes of interest in a solvent by introducing into the mixture a linear polymer having a molecular weight effective to form an entangled polymer network into which the sample mire is embedded. The network or matrix has a mesh size effective to retard movement of the macrobiomolecules through the matrix when an electric field is applied in a direction to draw the biomolecules in one direction through the matrix.

The macrobiomolecules include proteins, or nucleic acids, particularly genomic DNA, nucleic acid sequencing templates, or PCR products, and generally have a molecular weight of at least 5000 Daltons. For DNA sequencing templates of at least about 2000 bases or base-pairs, the molecular weight is at least about $6\times10^5$ Daltons.

More particularly, the method of entrapping DNA sequencing template macromolecules in a sample mixture in accordance with the invention comprises the steps of:

a) providing a liquid nucleic acid sequencing sample mixture containing at least a DNA template macromolecule, a DNA extension product, and a solvent, and b) introducing a linear polymer capable of formulating an open entangled polymer network in the mixture containing the DNA template and DNA extension products wherein the network has sieving properties effective to restrict movement of only large biomolecular fragments having a size greater than about 2000 bases.

The present invention is particularly suited for sequencing of nucleic acid fragments electrophoretically in an elongated separation medium such as a gel in a capillary tube. The method for sequencing a nucleic acid sequence such as a DNA sequence in accordance with the invention comprises the steps of:

a) generating a mixture of partial-sequence nucleic acid fragments in a fragment mixture also containing relatively high molecular weight template nucleic acid molecules;

b) embedding the fragment mixture in a polymer matrix effective to preferentially retard the movement of the template nucleic acid molecules through the matrix, when an electric field is placed across the matrix;

c) placing the matrix and embedded mixture in communication with one end region of an elongate electrophoretic medium effective to resolve such partial-sequence fragments, when an electric field is placed across the end regions of the medium;

d) applying an electric field between the matrix and other end region of said medium, in a direction which draws nucleic acid fragments through the matrix and into and through the medium, whereby a substantial increase in the amount of partial sequence fragments entering the electrophoresis medium can be achieved.

An electrophoretic system in accordance with the invention for use in sequencing a nucleic acid fragment, by electrophoretic separation of a mixture of partial-sequence nucleic acid fragments in a fragment mixture also containing relatively high molecular weight template nucleic acids, comprises:

1) A polymer matrix effective to preferentially retard the movement of the template nucleic acids through the matrix, when such a mixture is embedded in the matrix and an electric field is placed across the matrix;

2) an elongate electrophoretic medium effective to resolve such partial-sequence fragments, when an electric field is placed across the end regions of the medium, the medium having one end in communication with said matrix; and 3) means for applying an electric field between the matrix and the other end region of the medium in a direction which draws nucleic acid fragments through the matrix and into and through the medium.

This means may be a constant D.C. voltage or a pulsed voltage source, as is generally used in capillary electrophoresis.

Figure 6:
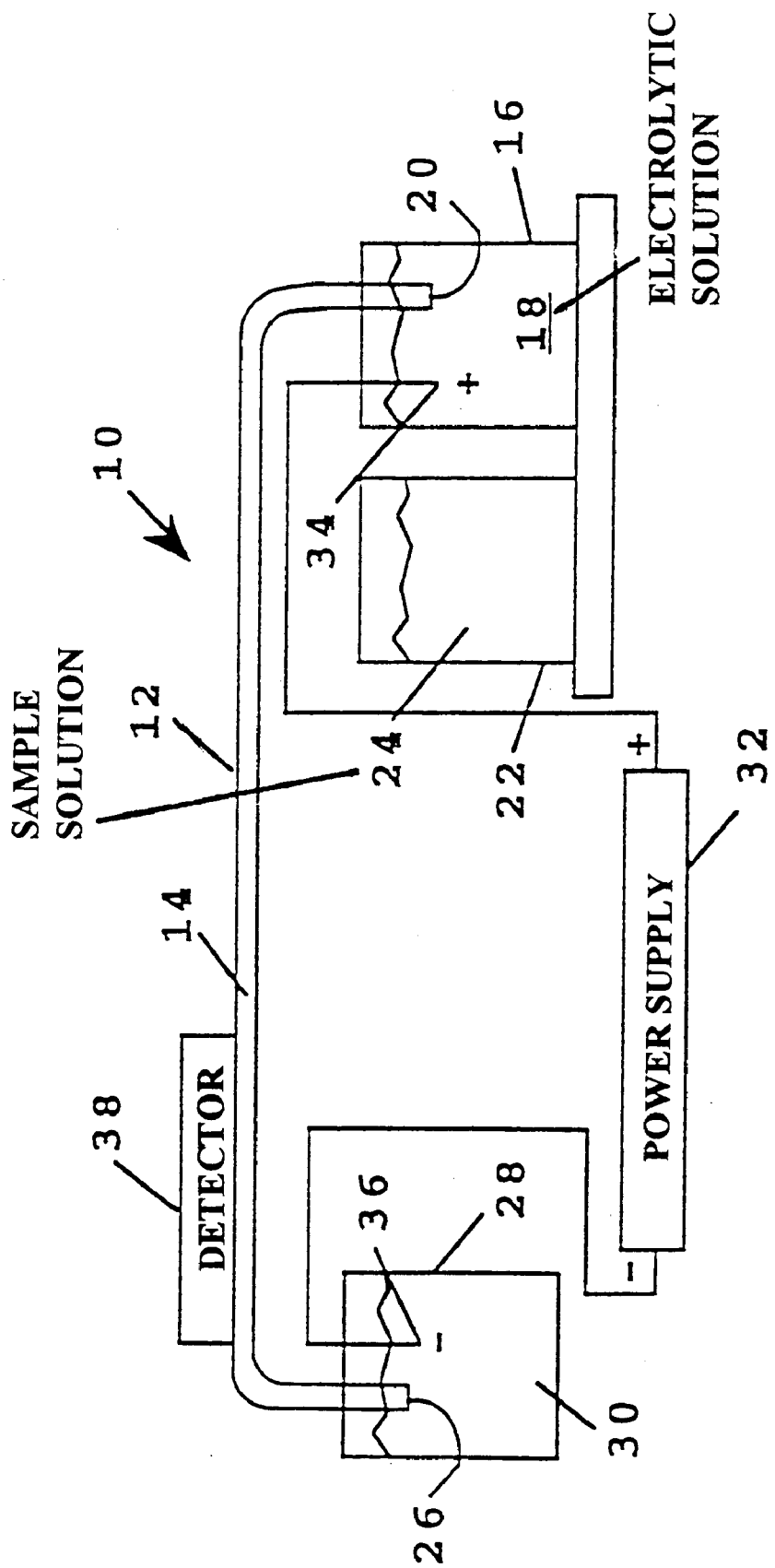
FIG. 6 is a simplified schematic view of a system in accordance with the invention.

A simplified schematic view of a capillary electrophoresis system suitable for practicing the method of the invention is shown in FIG. 6. The system 10 includes a capillary-tube 12 supporting a separation medium 14. This medium may be an entangled polymer, a gel, or any other separation medium such as has been previously described. An anodic container or reservoir 16 in the system contains an electrolytic solution 18. The anodic end of the tube, indicated at 20, is immersed in the sample solution, as shown, during electrophore. A reservoir 22 in the system may contain a marker solution, or may contain a sample solution 24 of biomolecules to be separated, during an electrophoretic separation. This sample solution includes the entangled polymer matrix to retard movement of the large macrobiomolecule in the sample. The two anodic reservoirs may be carried on a carousel or the like, for placement at a position in which the lower anodic end 20 of the tube 12 can be immersed in the reservoir fluid (18 or 24). Although not shown here, the carousel may carry additional reservoirs containing, solutions for cleaning and flushing the tube between electrophoretic runs or different solutions, where two or more solutions are employed in a single electrophoretic fractionation method.

The opposite, cathodic end 26 of the tube 12, is sealed within a cathodic reservoir 28 and is immersed in an cathodic electrolyte solution 30 contained in the reservoir 28, as shown.

A high voltage supply 32 in the system 10 is connected to the anodic and cathodic reservoirs 18 and 28 as shown, for applying a selected electric potential between the two reservoirs. The power supply leads are connected to platinum electrodes 34, 36 in the anodic and cathodic reservoirs, respectively. The power supply may be designed for applying a constant voltage. (DC) across the electrodes, preferably at a voltage setting of between 5–50 kV. Alternatively, or in addition, the power supply may be designed to apply a selected frequency, pulsed voltage between the reservoirs. In general, the shorter the capillary tube, the higher the electric field strength that can be applied, and the more rapid the electrophoretic separation.

When operated in a pulsed voltage mode, the power supply preferably outputs a square wave pulse at an adjustable frequency of about 50 Hz up to a KHz range, and an rms voltage output of about 10–30 KV. Higher pulse frequencies, even into the MHz range may be suitable for some applications.

Completing the description of the system shown in FIG. 6, a detector 38 in the system is positioned adjacent the cathodic end of the tube, for optically monitoring nucleic acid fragments migrating through an optical detection zone 40 in the tube. The detector may be designed either for UV absorption detection and/or for fluorescence emission detection. UV absorbance is typically carried out at 205–280 nm, using, for example, a Kratos 783 UV absorbance detector which has been modified by Applied Biosystems (Foster City, Calif.), by replacing the flow cell with a capillary holder. Fluorescence emission detection is preferably carried out at a selected excitation wavelength which is adjustable between about 240–500 nm, depending on the fluorescent species associated with the nucleic acid fragments, as discussed below one exemplary fluorescence detector is an HP1046A detector available from Hewlett-Packard (Palo Alto, Calif), and modified as above for capillary tube detection. The detector is connected to an integrator/plotter 45 for recording electrophoretic peaks.

In an additional aspect of the present invention, Applicants have discovered that lactams, i.e., cyclic arnides, and lactones, i.e., cyclic esters, are preferred denaturants for nucleic acids subjected to high-resolution electrokinetic separations. This property may stem from their unusual effectiveness as solvents for aromatic molecules, combined with their high solubility in water. These two features permit the formation of aqueous electrolyte solutions which also effectively dissolve the aromatic nucleic acid bases, thereby disrupting any base stacking interactions in the nucleic acid. Lactams are preferred over lactones as nucleic acid denaturants because of their superior stability in aqueous solution. Preferred nucleic acid denaturants are N-alkyl pyrrolidones, e.g., N-ethyl-pyrrolidone, N-hydroxyethyl pyrrolidone, and N-cyclohexylpyrrolidone, δ-valerolactar, ε-caprolactam, and N-methyl-ε-caprolactam. More preferred lactams are 2-pyrrolidinone and 1-methyl-2-pyrrolidinon. Relative practical value of the various lactams rests on such properties as melting point, density, aqueous solubility, and purity of commercially available material, and may vary from application to application. N-methylpyrrolidone and 2-pyrrolidinone are preferred over the conventional nucleic acid denaturants, formanride and urea, not only because of their greater resistance to hydrolysis, but also because they are more effective, on a per-gram or per-mole basis, in denaturing DNA. These benefits can improve at least two classes of reagents for electrokinetic separations; the sample loading solvent used to introduce the nucleic acid into the separation apparatus and the medium through which the nucleic acid travels during the separation. In fact, these benefits permit, for the first time, the commercial sale and distribution of ready-to-use reagents for the electrokinetic separation of nucleic acids under denaturing conditions.

For the case of nucleic acid separations, it is preferred to also include a chelator in the denaturing solvent. The chelator serves primarily to prevent excess $Mg^{+2}$ from binding to the nucleic acid, thereby changing its conformation and solubility. Preferred chelators include ethylenediaminetetra acetic acid (EDTA), ethylene glycol-bis(β-aminoethyl ether N,N,N',N'-tetraacetic acid (EGTA), N,N-bis[2-(bis[carboxymethyl]amino)ethyl]-glycine (DTPA), triethylenetetraaminehexaacetic acid (TTHA), and trans-1,2-diaiocyclohexane (CDTA). A more preferred chelator is trans-1,2-diaminocyclohexane (CDTA).

One preferred example of a sample solution containing a sample mixture embedded in an entangled polymer matrix in accordance with the invention is a sample mixture containing DNA templates and primer extension products, a long linear polymer such as hydroxyethyl cellulose (HEC) with a molecular weight of about $4 \times 10^6$ Daltons (such as Union Carbide QP100MH) dissolved in a solvent comprising 2-pyrrolidinone, water, and a magnesium chelator, e.g., EDTA, the polymer concentration being adjusted to a value that restricts electrophoretic mobility of the macrobiomolecule. An effective minimal concentration of the linear polymer in the solution mixture is between 0.1 to about 0.2 percent. This concentration results in successful injection times of at least 40 seconds at 4.5 kV. This is a factor of 8 increase over conventional electrokinetic injection times. A preferred solvent is between 10%(wt/wt) and 70%(wt) 2-pyrrolidinone in water.

EXAMPLES

The following examples are presented to illustrate the invention and are not intended to limit in any way the scope of the invention.

Example 1

A type DB-1 capillary tube, obtained from J and W Scientific, Folsom, Calif. Catalog No. 126-1013, was prepared and cut into 50 centimeter lengths. The tubing had an internal diameter of 50 mm. The capillary was then rinsed with methanol and water. The capillary was then hydrodynamically filled with a polyethylene glycol (PEG)/fluorinated copolymer gel consisting of 7% C4F9/Carbowax 4600 in 125 mM borate—tetramethyl ammonium hydroxide (TMA), 1.25 mM of EDTA, 6.6 molar urea and a pH of 9.0 at standard conditions. The 50 cm capillary tube was filled half full in 8 minutes, and fully filled in 32 minutes.

The first sample was a control sample, without the entangled polymer in the sample solution. A single color sequencing ladder of fragments terminating at C was prepared by the dideoxy sequencing method using a sequencing kit and accompanying protocols from Applied Biosystems (part No. 401119). An M13mpl8 DNA template (ml3mpl8 (+)strand, 0.1 pmole) was annealed to a fluorescent dye primer (FAM M13 (−21) primer, and primer extension was carried out using Taq polymerase, with dideoxycytidine provided as the 31-terminating base.

The sample was prepared in a vial containing 5 $\mu$l of formainide and 0.5 $\mu$l of 25 mM sodium EDTA, pH of 9. The sample contained the reactants from F.AM Taq M13 (−21) primer sequence of 0.5 pg M13 template DNA dissolved in the 5 $\mu$l of formamide plus 2.5 mM EDTA The sample was then heated at 90° C. for 2 minutes. Prior to the electrokinetic injection, a preconditioning run was done at 9 kV, 5.8 $\mu$A on the tube. The electrokinetic sample injection was performed at 0.4 $\mu$A, 0.9 kV, for 60 seconds to achieve a charge total of 24 $\mu$Coulombs. The resultant electropherogram is shown in FIG. 1.

Example 2

Figure 2:
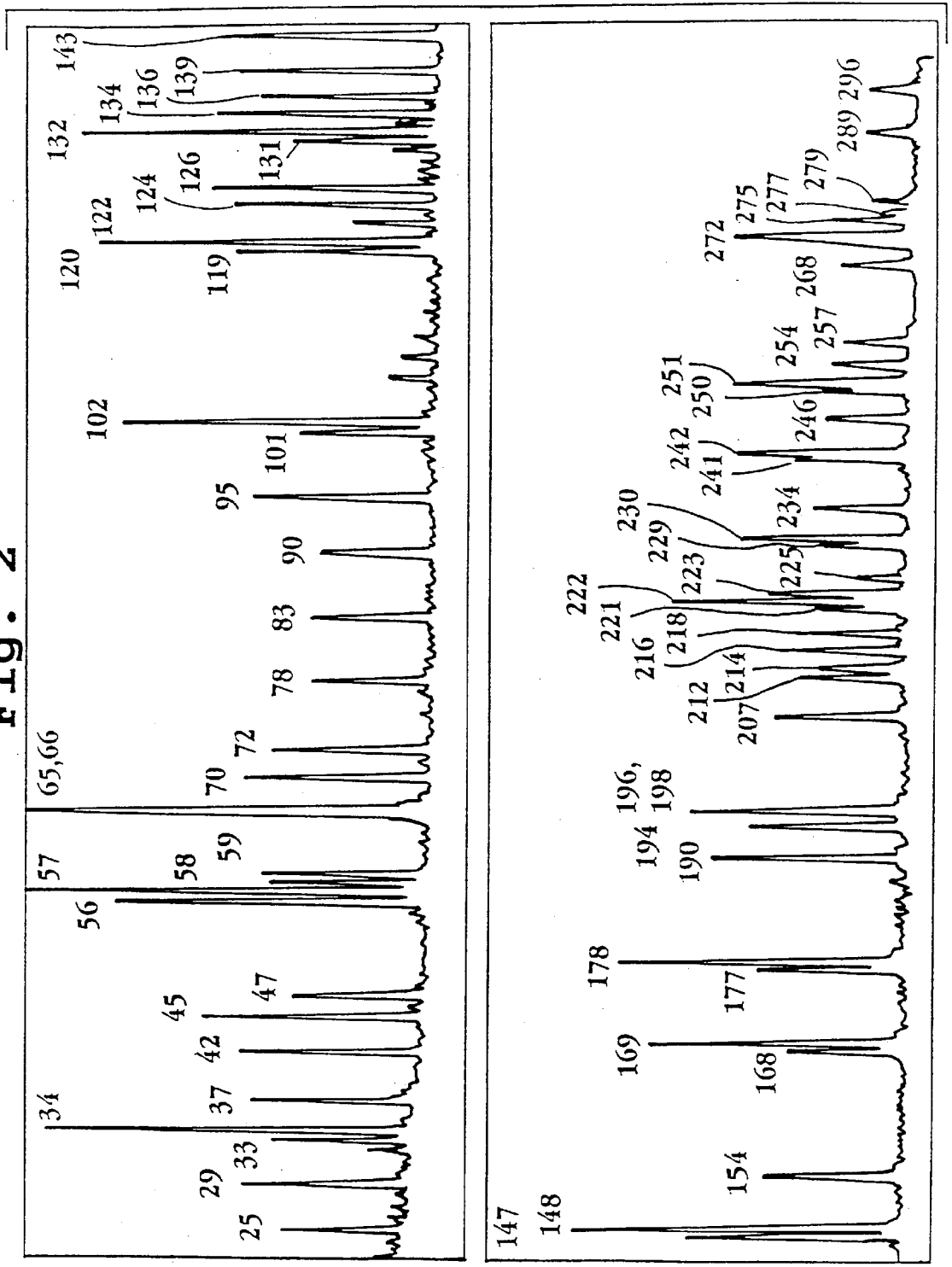
FIG. 2 is a first part of the electropherogram of the results of Example 2.
Figure 3:
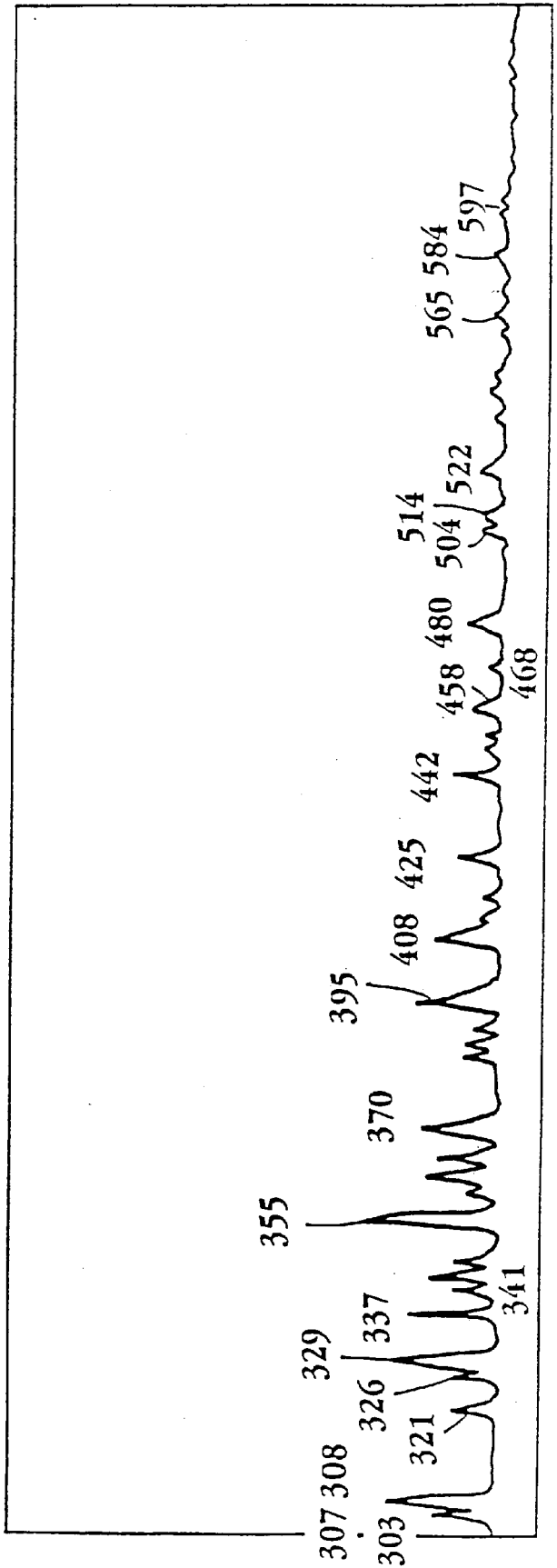
FIG. 3 is the second part of an electropherogram of the results of Example 2.

A capillary tube section 50 cm in length and 50 $\mu$m in diameter was prepared as above described in Example 1 with a 7% gel made of C4F9/Carbowax 4600 in 125 mM boric acid-TMA, 1.25 mM EDTA, 6.6 molar urea, and a pH of 9.0. The sample in this case was the reactants from FAM Taq M13 (−21) primer sequence of 0.5mg M13 template DNA dissolved in 5 $\mu$l of formarnide 0.5 $\mu$l 25 mM sodium EDTA, plus 0–1% QP10OMH HEC (hydroxyethyl cellulose). The sample solution was heated to 90° C. for 2 minutes, and then electrokineticaily injected into the capillary tube at 4.5 kV, 3 $\mu$A, for 20 seconds. The resultant electropherogram is shown in FIGS. 2 and 3.

Example 3

Figure 4:
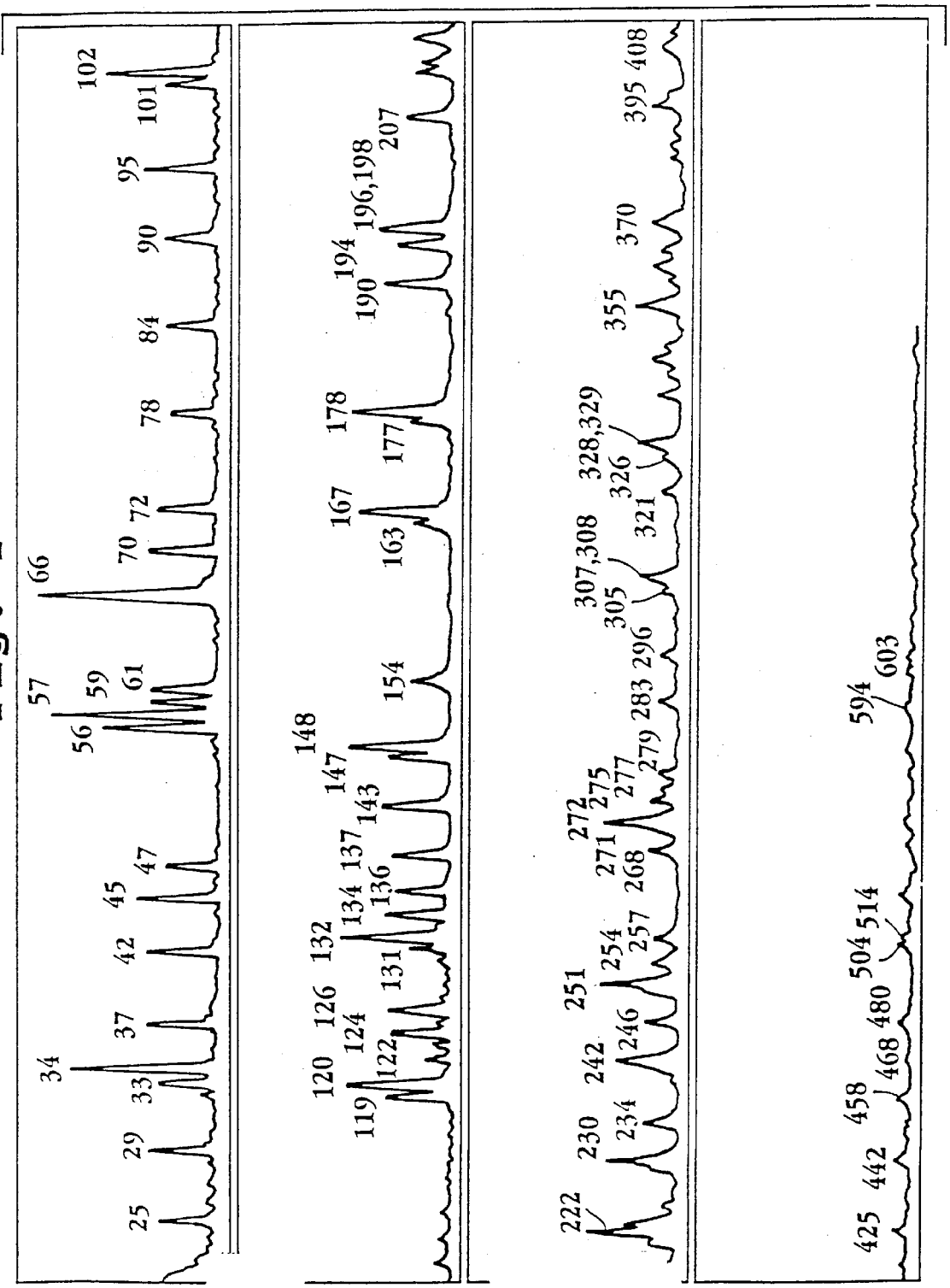
FIG. 4 is an electropherogram of the results of Example 3.

A capillary tube 50 cm in length and 50 $\mu$m in diameter was prepared with a 7% gel made of C4F9/Carbowax 4600 in 125 mM borate-TMA, 1.25 mM sodium EDTA, 6.6 molar urea, and a pH of 9.0. The sample in this case was the reactants from FAM Taq M13 (−21) primer sequence of 0.5 pg M13 template DNA dissolved in 5 $\mu$l of formamide plus 5 $\mu$l of 25 mM sodium EDTA, plus 0.15% QP 1OOMH HEC. The sample solution was heated to 90° C. for 2 minutes, and then electrokinetically injected into the capillary tube at 4.5 kV, 3 $\mu$A, for 20 seconds. The results of this experiment are shown in FIG. 4.

Example 4

Figure 5:
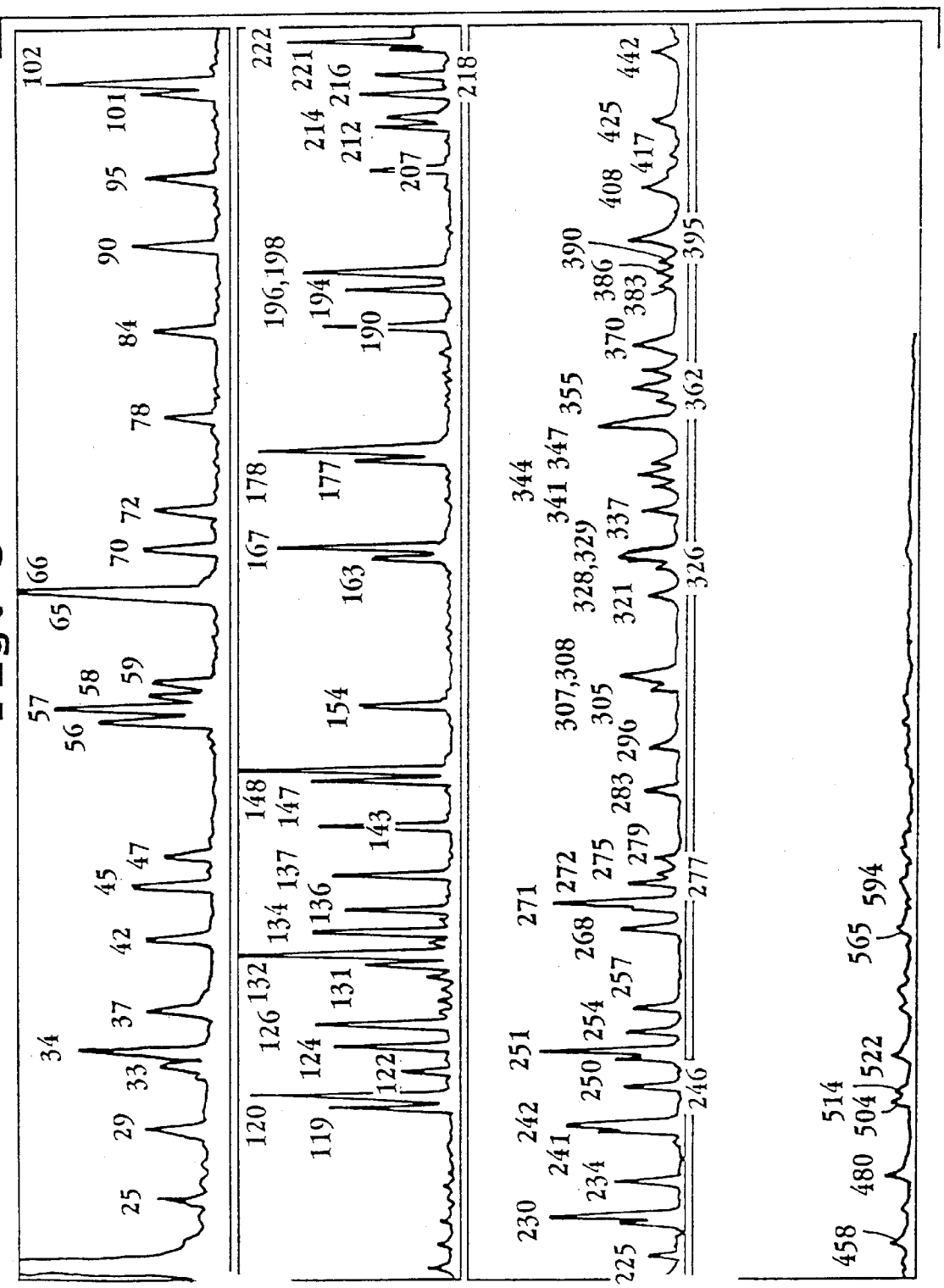
FIG. 5 is an electropherogram of the results of Example 4.

A capillary tube 50 cm in length and 50 $\mu$m in diameter was prepared with a 7% gel made of C4F9/Carbowax 4600 in 125 mM borate-TMA, 1.25 mM EDTA, 6.6 molar urea, and a pH of 9.0. The sample in this case were the reactants from FAM Taq M13 (−21) primer sequence of 0.5 mg M13 template DNA dissolved in 5 $\mu$l of formamide plus 0.5 $\mu$l of 25 mM sodium EDTA, plus 0.15% QP10OMH HEC—The sample solution was heated to 90° C. for 2 minutes, and then electrokinetically injected into the capillary tube at 4.5 kV, 3 $\mu$A, for 40 seconds. The results of this experiment are shown in FIG. 5.

The electropherograms in FIGS. 1 through 5 plot signal amplitude versus time. The amplitude of signal is generally proportional to the quantity of analyte injected. The numbers above the peaks indicate the number of basepairs in the segment. The sample mixture in Example 1 was a control which did not contain an entangled polymer as in the other examples. It can be readily seen that the quantity of DNA extension products introduced into the capillary tube is substantially greater in each of Examples 2, 3, and 4, shown in FIGS. 2 through 5 compared to the control sample injection reflected in FIG. 1. The amplitudes in the control electropherogram (FIG. 1) are at least about an eighth to a tenth that of the examples containing the QP10OMH HEC entangled polymer.

Example 5

The following Example describes the preparation of a stable denaturing loading solvent appropriate for use with slab gel electrophoresis of nucleic acids.

To 2.42 g of trans-1,2-diaminocyclohexane-N,N;N',N'-tetraacetic acid (CDTA; Sigma Chemical Co. St. Louis, Mo.) were added enough 10% tetramethyl ainmonium hydroxide (TMAH; SA Chemn, Inc., Cleburne, Tex.) to give a clear solution oftotal volume 9.0 ml and a concentration of 0.77 M of the tetramethylammonium salt of CDTA (TMA-CDTA). Four hundred mg of Oil Blue N (Sigma Chemical Co.) were dissolved in 9.6 g 2-pyrrolidinone (Aldrich Chemical Co., Milwaukee, Wis.) to make a 4% solution. Dye solids which settled from this solution when the ambient temperature dropped below 25° C. were easily resuspended by repeated mversion of the storage vial. This and all other solutions of 2-pyrrolidinone (or NMP) were stored in glass containers to avoid leaching of fluorescent impurities which occurred upon storage in plastic containers.

To 975 $\mu$l 2-pyrrolidinone were added 15 $\mu$l 0.77 M TMA-CDTA and 10 $\mu$l 4% Oil Blue N (see above) to give 1.00 ml of Loading Reagent A: 0.04% Oil Blue N, 11.6 nM TMA-CDTA, 1.5% $H_2O$, 98.5% 2-pyrrolidinone. Loading Reagent A is stable indefinitely at 20–30° C.

To 210 $\mu$l of Loading Reagent A were added 30 $\mu$l of GeneScin 2500-TANRA fluorescent electrophoretic size standards (Applied Biosystems Division of Perkin Elmer, Foster City, Calif.) to give 240 $\mu$l of Loading Reagent B: 0.035% Oil Blue N, 10.2 nm TMA-CDTA, 132. H2O, 86% 2-pyrrolidinone, and a 12.5% dilution of GeneScan 2500-TAMRA size standards. Loading Reagent B was stable for a least 2 weeks at 20–30° C. and indefinitely at 4° C. A solid hydrate of 2-pyrrolidinone precipitated at 4° C. but was easily redissolved by agitating the storage container in hot tap water.

To prepare a nucleic acid sample for loading on a denaturing electrophoretic slab gel, 4 $\mu$l of Loading Regent B were mixed with 3 $\mu$l of nucleic acid sample (e.g., the reaction mixture from a completed Polymerase Chain Reaction [PCR] or Oligonucleotide Ligation Assay [OLA] in a 200 $\mu$l microcentrifuge tube (MicroAmp Tube, Perkin Elmer, Norwalk, Conn.) and heated for 2 minutes at 98° C. in a Model 9600 GeneAmp PCR System 9600 (Perkin Elmer). Usually 24 such loading samples were prepared simultaneously, enough to fill completely the lanes of one electrophoretic gel. The final 2-pyrrolidinone concentration in this loading sample was 49%, providing better DNA denaturing capacity then 50% urea or formanide. The CDTA concentration sufficed to neutralize $Mg^{+2}$ concentrations in the 3 µl test sample of up to 13.6 mm; PCR and OLA customarily contain $Mg^{+2}$ concentrations no higher than 10 mm. Five µl volumes of the loading samples were applied to the sample wells of thin, i.e., 250 µm thickness, 6% or 8% polyacrylarnide gels containing 50% urea and were electrophoresed in a 373A Automated DNA Sequencer (Applied Biosystems) according to the instructions for that instrument. The electropherograms were analyzed using GENES-CAN 672 Software (Applied Biosystems) according to the software instructions. The peaks of fluorescently tagged DNA fragments (both size standards and PCR products) showed identical resolution and sensitivity to peaks obtained when the conventional loading reagents, containing formnamide as a denaturant and ethylenediaminetetraacetic acid (EDTA) as a $Mg^{+2}$ chelator. However, because of poor stability, the conventional loading reagents had to be formulated shortly before use. Furthermore, the final mixture of DNA sample and Loading Reagent B could be stored for several days at 20–30° C. before application to the gel. Such storage is not advised for conventional formarnide formulations, again because of hydrolytic lability of the formamide. When formamide or urea are hydrolyzed, the resulting salts (ammonium formate or ammonium caronate) increase electrical conductivity of the loading sample in a way which can seriously degrade electrophoretic resolution. If formamide or urea are used in the buffer in which a polyacrylamide gel is poured, denaturant hydrolysis results in excessive electrical current and heating during the electrophoretic run. Moreover, the denaturant hydrolyisis products result in a time-varying current in the gel which can lead to severe reproducibility problems.

While the invention has been described with reference to particular embodiments thereof it should be apparent that the sample composition in the method may be practiced other than as specifically described. Various polymers and copolymers may be utilized to retard or inhibit movement of the DNA sequencing template in the system and method in accordance with the invention provided that the polymers or copolymers form an entangled polymer matrix in which the sample is embedded.

In addition to the polymers above described which may be used in the invention, the concentration of the polymers or copolymers in the sample mixture will affect the mobility of the macromolecules such as the DNA sequencing templates. For example, when a high molecular weight HEC such as QP100MH HEC is utilized, an effective minimum concentration is 0.1% to 0.2%. Where a different polymer is used, the concentration must be varied to optimize the mobility restriction without affecting mobility of the analytes of interest.

The embodiments of the invention are subject to modification, variation, and change without departing from the proper scope and fair meaning of the appended claims. Accordingly, it is intended to embrace all such changes, modifications, and variations that fall within the spirit and broad scope of the appended claims. All patents, patent applications, and publications cited herein are hereby incorporated by reference in their entirety.

What is claimed is:

1. A denaturing solvent useful for the electrophoresis of nucleic acids comprising:

an entangled polymer formed by a linear polymer; and a denaturant selected from the group consisting of N-alkyl pyrrolidinone, δ-valerolactam, N-methyl-caprolactam, and lactone.

2. The denaturing solvent of claim 1 wherein the N-alkyl pyrrolidinone is 2-pyrrolidinone.

3. The denaturing solvent of claim 1 wherein the linear polymer is linear polyacrylamide.

4. The denaturing solvent of claim 1 wherein the linear polymer is selected from the group consisting of N,N-disubstituted polyacrylamides and N-substituted polyacrylamides.

5. The denaturing solvent of claim 4 wherein the N,N-disubstituted polyacrylamides and N-substituted polyacrylamides are substituted with substituents selected from the group consisting of $C_1$ to $C_3$ alkyl, halo-substituted $C_1$ to $C_3$ alkyl, methoxy-substituted $C_1$ to $C_3$ alkyl, and hydroxy-substituted $C_1$ to $C_3$ alkyl.

6. The denaturing solvent of claim 5 wherein the substituent is methyl.

7. The denaturing solvent of claim 1 wherein the linear polymer is hydroxyethylcellulose.

* * * * *